United States Patent [19]

Stockinger et al.

[11] 4,302,573
[45] Nov. 24, 1981

[54] METAL SALT/AMINE COMPLEXES AS EPOXY RESIN CATALYTIC CURING AGENTS

[75] Inventors: Friedrich Stockinger, Hölstein; Sameer H. Eldin, Birsfelden; Friedrich Lohse, Oberwil, all of Switzerland

[73] Assignee: Ciba-Geigy Corporation, Ardsley, N.Y.

[21] Appl. No.: 147,682

[22] Filed: May 7, 1980

Related U.S. Application Data

[62] Division of Ser. No. 956,520, Oct. 31, 1978, abandoned.

[30] Foreign Application Priority Data

Nov. 4, 1977 [CH] Switzerland .................. 13446/77

[51] Int. Cl.³ ............................................ C08G 59/70
[52] U.S. Cl. .............................. 528/89; 260/239.3 R; 260/326.22; 260/429 J; 260/438.1; 260/439 R; 525/507; 528/90; 528/92; 528/361; 528/409; 528/410; 528/412; 528/414
[58] Field of Search .................. 528/92, 89, 361, 90, 528/409, 412, 410, 414; 525/507

[56] References Cited

U.S. PATENT DOCUMENTS

| | | | |
|---|---|---|---|
| 2,686,798 | 8/1954 | Gmitter | 260/429.9 |
| 2,819,233 | 1/1958 | Smith et al. | 528/92 X |
| 3,058,948 | 10/1962 | Mosimann et al. | 260/44 |
| 3,397,157 | 8/1968 | Holmes | 528/92 |
| 3,576,012 | 4/1971 | Matlack | 260/345.2 |
| 3,786,079 | 1/1974 | Yozinawa | 260/438.1 |
| 4,025,526 | 5/1977 | Suzuki et al. | 260/302 R |
| 4,237,242 | 12/1980 | Frankel | 525/119 |

FOREIGN PATENT DOCUMENTS

| | | |
|---|---|---|
| 484299 | 5/1938 | United Kingdom. |
| 486109 | 5/1938 | United Kingdom. |
| 871144 | 6/1961 | United Kingdom. |
| 871145 | 6/1961 | United Kingdom. |
| 1282460 | 7/1972 | United Kingdom. |
| 1470463 | 4/1977 | United Kingdom. |

*Primary Examiner*—Earl A. Nielsen
*Attorney, Agent, or Firm*—Harry Falber

[57] ABSTRACT

Novel carboxylic acid metal salt/amine complexes are prepared by reacting 1 mol of a carboxylic acid metal salt of the formula

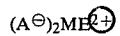

in which $A^\ominus$ is the anion of a carboxylic acid which contains polar substituents or radicals and in particular contains an amide or imide grouping, such as a halogenoacetic acid, nitrilo-, cyano- or ureido-acetic acid, monoamidosuccinic acid, succinimidyl- or maleimidyl-alkanecarboxylic acid, benzenesulphonic acid or pyrrolidone-5-carboxylic acid, and $Me^{\oplus}$ is a divalent metal cation, with 1 mol of a diamine of the formula

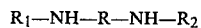

in which R is an aliphatic radical having not more than 7 C atoms or is a cycloaliphatic radical and $R_1$ and $R_2$ are hydrogen, alkyl having 1 to 4 C atoms, cyclohexyl, benzyl, 2-aminoethyl or 3-aminopropyl, in a polar organic solvent and in the temperature range from 25° to 200° C., to give complex compounds. The novel complex compounds are suitable as catalytic curing agents for epoxide resins.

6 Claims, No Drawings

METAL SALT/AMINE COMPLEXES AS EPOXY RESIN CATALYTIC CURING AGENTS

This is a divisional of application Ser. No. 956,520 filed on Oct. 31, 1978, now abandoned.

The present invention relates to metal salt/amine complexes, a process for their preparation and the use of the novel complex compounds as catalytic curing agents for epoxide resins.

It is known to cure epoxide resins with catalytically active curing agents, such as boron trifluoride/amine complexes or tertiary amines. When mixed with epoxide resins, the $BF_3$/amine complexes have a long pot life, which is advantageous for further processing, but they give moulded materials which have low mechanical strengths and in particular poor dielectric properties. Mixtures of epoxide resins with tertiary amines are not stable on storage and because of their short pot life are not suitable for many applications.

Metal complexes of aliphatic carboxylic acids with diethylenetriamine and their use as curing agents for epoxide resins are known from U.S. Pat. No. 2,819,233. However, these known metal complexes also have the disadvantage that they have a relatively low stability on storage when mixed with epoxide resins. Moreover, relatively long curing times are required for complete crosslinking of the epoxide resin mixtures containing these complexes.

In Japanese Patent Publication No. 24,397/75 it is also proposed to cure epoxide resins with a curing agent combination consisting of salts of aliphatic carboxylic acids and amines. This curing agent combination does indeed have good storage stability when mixed with epoxide resins, but the curable mixtures give moulded materials which have low mechanical strengths and poor dielectric properties.

It has now been found that metal salts of organic carboxylic acids which contain polar substituents or radicals and in particular contain an amide or imide grouping can be reacted with specific diamines to give complex compounds which do not have the disadvantages described above or have the disadvantages to a lesser extent. The storage stability of the novel complex compounds when mixed with epoxide resins is far better, and the cured moulded materials have better mechanical and especially dielectric properties.

The present invention thus relates to novel metal/amine complexes of the formula I

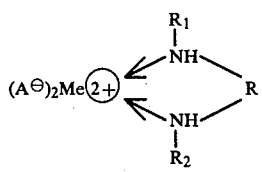

(I)

in which $A^\ominus$ is an acetate ion of a halogenoacetic acid or nitrilo-, cyano- or ureido-acetic acid or an anion of the formula II $$R_3-NH-CO-Y_1-COO^\ominus \quad (II)$$

in which $R_3$ is —H, alkyl having 1 to 4 C atoms, cyclopentyl or cyclohexyl and $Y_1$ is a radical of the formulae $(CH_2)_x$, in which $x=2$ or 3, or —CH=CH—, an anion of the formula III

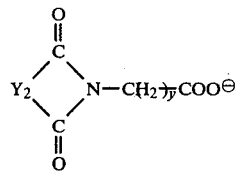

(III)

in which y is a number from 1 to 5 and $Y_2$ is ethylene, propylene, vinylene, dimethylvinylene,

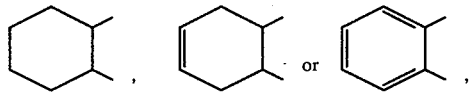

an anion of the formula IV $$R_4-CO-NH-(CH_2)_z COO^\ominus \quad (IV)$$

in which z is a number from 1 to 5 and $R_4$ is methyl or ethyl, or an anion of the formulae

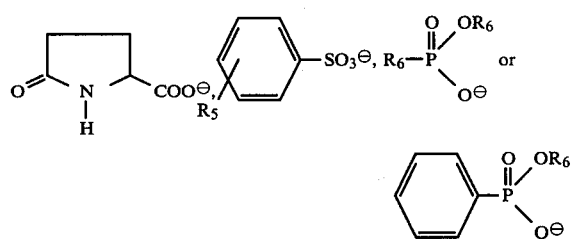

in which $R_5$ is —H or methyl and $R_6$ is an alkyl having 1 to 4 C atoms, $Me^{(2+)}$ is a divalent metal cation and, if $R_1$ and $R_2$ are each a hydrogen atom, R is one of the following radicals —$CH_2$—$(CH_2)_p$, in which p=a number from 1 to 6,

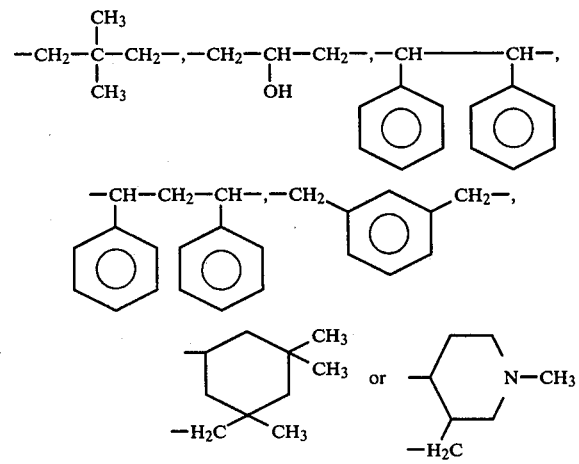

and, if $R_1$ is a hydrogen atom and $R_2$ is an alkyl having 1 to 4 C atoms, cyclohexyl, benzyl, 2-aminoethyl or 3-aminopropyl, or if $R_1$ and $R_2$ are each an alkyl having 1 to 4 C atoms, cyclohexyl or benzyl, R is an ethylene or propylene radical.

Preferably, $A^\ominus$ in formula I is an acetate ion of a halogenoacetic acid or nitrilo- or ureido-acetic acid or an anion of the formula II

 (II)

in which R$_3$ is —H, alkyl having 1 to 4 C atoms, cyclopentyl or cyclohexyl and Y$_1$ is a radical of the formulae —(CH$_2$)$_x$, in which x=2 or 3, or —CH=CH—, an anion of the formula III

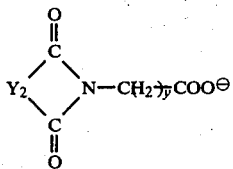 (III)

in which y is a number from 1 to 5 and Y$_2$ is ethylene, propylene, vinylene, dimethylvinylene,

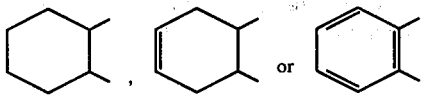

an anion of the formula IV

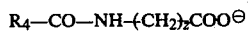 (IV)

in which z is a number from 1 to 5 and R$_4$ is methyl or ethyl, or an anion of the formulae

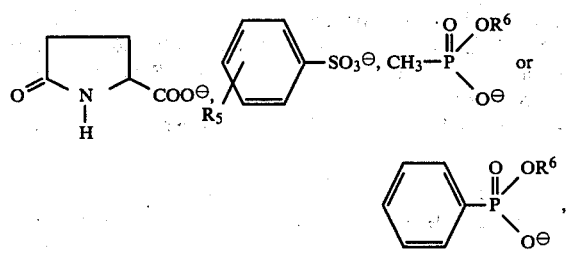

in which R$_5$ is —H or methyl and R$_6$ is an alkyl having 1 to 4 C atoms, Me$^{(2+)}$ is a divalent metal cation and, if R$_1$ and R$_2$ are each a hydrogen atom, R is one of the following radicals —(CH$_2$—CH$_2$)$_p$, in which p=a number from 1 to 6,

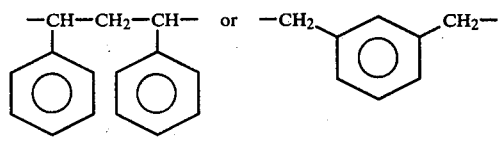

and, if R$_1$ is a hydrogen atom and R$_2$ is an alkyl having from 1 to 4 C atoms, cyclohexyl, benzyl, 2-aminoethyl or 3-aminopropyl, or if R$_1$ and R$_2$ are each an alkyl having 1 to 4 C atoms, cyclohexyl or benzyl, R is an ethylene or propylene radical.

In particular, A$^{\ominus}$ in formula I is an anion of the formula II or of the formulae

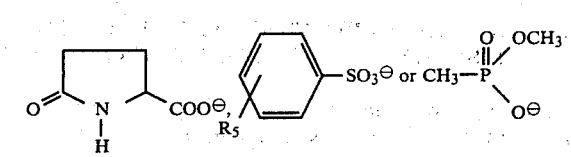

In a particularly preferred embodiment, A$^{\ominus}$ in formula I is an anion of the formula II in which R$_3$ is —H, alkyl having 1 to 4 C atoms or cyclohexyl and Y$_1$ is a radical of the formula —(CH$_2$)$_x$, in which x is 2 or 3, or an anion of the formulae

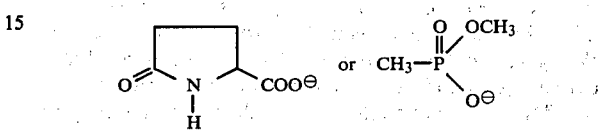

Preferred compounds of the formula I in which A$^{\ominus}$ is an acetate ion of a halogenoacetic acid, such as chloro- or trifluoro-acetic acid, or of nitrilo-, cyano- or ureidoacetic acid are those in which A$^{\ominus}$ is the acetate ion of chloroacetic acid or ureidoacetic acid.

Compounds of the formula I in which Me$^{(2+)}$ is a divalent cation of Zn, Co, Cu, Ni or Cd, especially Zn, are also preferred compounds.

Furthermore, preferred amine complexes of the formula I are those in which R$_1$ and R$_2$ are each a hydrogen atom and R is a radical of the formulae —CH$_2$—CH$_2$)$_p$, in which p=a number from 1 to 6,

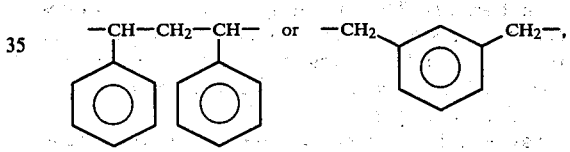

or in which R$_1$ is a hydrogen atom and R$_2$ is cyclohexyl, benzyl, 2-aminoethyl or 3-aminopropyl and R is an ethylene or propylene radical.

In particular, in the formula I, R$_1$ and R$_2$ are each a hydrogen atom and R is a radical of the formula —CH$_2$—CH$_2$)$_p$, in which p is a number from 1 to 3, preferably 1 or 2, or R$_1$ is a hydrogen atom and R$_2$ is a cyclohexyl, benzyl, 2-aminoethyl or 3-aminopropyl and R is an ethylene or propylene radical.

The novel metal salt/amine complexes of the formula I are obtained by reacting 1 mol of an acid metal salt of the formula V

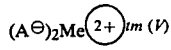 (V)

in which A$^{\ominus}$ and Me$^{(2+)}$ are as defined in formula I, with 1 mol of a diamine of the formula VI

 (VI)

in which R, R$_1$ and R$_2$ are as defined in formula I, in a polar organic solvent and in the temperature range from 25° to 200° C., preferably 50° to 150° C., to give the complex compounds of the formula I.

Acid metal salts of the formula V preferably used in this process are those in which A$^{\ominus}$ is an acetate ion of a halogenoacetic acid or nitrilo- or ureido-acetic acid or an anion of the formula II

  (II)

in which $R_3$ is —H, alkyl having 1 to 4 C atoms, cyclopentyl or cyclohexyl and $Y_1$ is a radical of the formulae —(CH$_2$)$_x$—, in which x=2 or 3, or —CH=CH—, an anion of the formula III

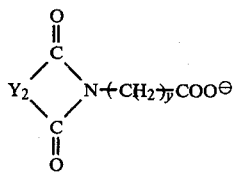  (III)

in which y is a number from 1 to 5 and $Y_2$ is ethylene, propylene, vinylene, dimethylvinylene,

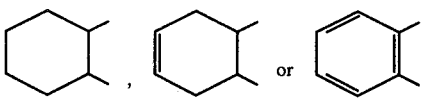

an anion of the formula IV

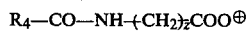  (IV)

in which z is a number from 1 to 5 and $R_4$ is methyl or ethyl, or an anion of the formulae

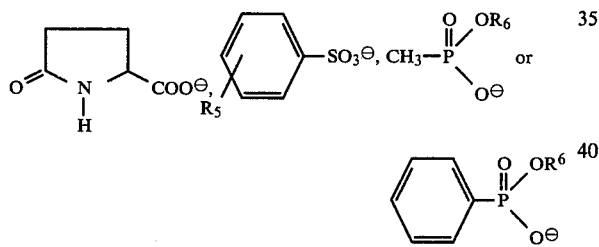

in which $R_5$ is —H or methyl and $R_6$ in each case is an alkyl having 1 to 4 C atoms, and Me$^{2+}$ is a divalent metal cation, and these salts are preferably reacted with 1 mol of a diamine of the formula VI

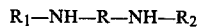  (VI)

in which, if $R_1$ and $R_2$ are each a hydrogen atom, R is one of the following radicals —(CH$_2$—CH$_2$)$_p$—, in which p=a number from 1 to 6,

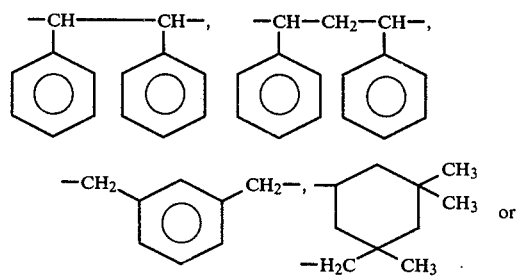

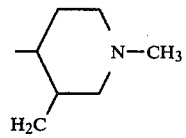

and, if $R_1$ is a hydrogen atom and $R_2$ is an alkyl having 1 to 4 C atoms, cyclohexyl, benzyl, 2-aminoethyl or 3-aminopropyl, or if $R_1$ and $R_2$ are each an alkyl having 1 to 4 C atoms, cyclohexyl or benzyl, R is an ethylene or propylene radical, in a polar organic solvent and in the temperature range from 25° to 200° C., preferably 50° to 150° C., to give the complex compounds of the formula I.

In particular, acid metal salts of the formula V used in this process are those in which A$^\ominus$ is an anion of the formula II or of the formulae

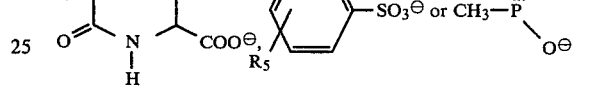

in which $R_5$ is —H or methyl and $R_6$ in each case is an alkyl having 1 to 4 C atoms.

In a preferred embodiment, the compounds of the formula V employed are those in which A$^\ominus$ is an anion of the formula II, in which $R_3$ is —H, alkyl having 1 to 4 C atoms or cyclohexyl and $Y_1$ is a radical of the formula —(CH$_2$)$_x$—, in which x is 2 or 3, or an anion of the formulae

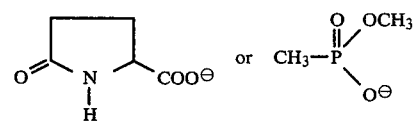

The acid metal salts of the formula V in which Me$^{2+}$ is a divalent metal cation of Zn, Co, Cu, Ni or Cd, especially Zn or Ni, are likewise compounds which are preferably used.

Diamines of the formula VI which are particularly preferentially employed are those in which $R_1$ and $R_2$ are each a hydrogen atom and R is a radical of the formulae —CH$_2$—(CH$_2$)$_p$—, in which p=a number from 1 to 5,

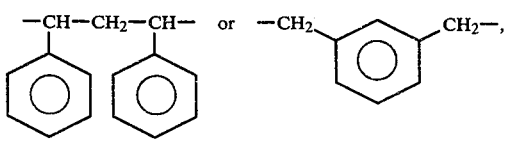

or in which $R_1$ is a hydrogen atom and $R_2$ is cyclohexyl, benzyl, 2-aminoethyl or 3-aminopropyl and R is an ethylene or propylene radical.

In particular, the diamines of the formula VI which are used are those in which $R_1$ and $R_2$ are each a hydrogen atom and R is a radical of the formula —CH$_2$—(CH$_2$)$_p$—, in which p is a number from 1 to 3, preferably 1 or 2, or in which $R_1$ is a hydrogen atom and $R_2$ is a cyclohexyl, benzyl, 2-aminoethyl or 3-aminopropyl and R is an ethylene or propylene radical.

The acid metal salts of the formula V can be obtained by reacting 2 mols of the corresponding organic acid with 1 mol of the corresponding metal oxide, with the elimination of water, or by reacting the Na salts of the organic acids with the corresponding metal salts of inorganic acids. A process of this type is described, for example, in "Helvetica Chimica Acta" 8, 1925, page 369–383.

The organic acids which contain the anions of the formula II, III or IV or of the other formulae cited are known compounds. Acids which contain the anion of the formula II are the amidoacids derived from succinic, glutaric, maleic or fumaric acid and also from dimethylmaleic acid. The amidoacids are obtained by reacting the said dicarboxylic acids, preferably the anhydrides thereof, with an amine of the formula $R_3$—$NH_2$, in which $R_3$ is as defined in formula II, in a molar ratio of 1:1 ("Houben-Weyl", Methoden der organischen Chemie (Methods of Organic Chemistry), volume 15/1, page 46 (1974)).

The acids which contain the anion of the formula III are imidoacids, which are obtained by reacting succinic anhydride, glutaric anhydride, maleic anhydride or dimethylmaleic anhydride with the corresponding ω-aminocarboxylic acids in a molar ratio of 1:1 (cf. Japanese Published Specification 74-107,046).

The ω-acylaminocarboxylic acids containing the anion of the formula IV are obtained in an analogous manner by reacting acetic acid or propionic acid with the corresponding ω-aminocarboxylic acids or ω-aminocarboxylic acid esters in a molar ratio of 1:1 (cf., for example, U.S. Pat. No. 2,956,068).

Compounds which contain an anion of the other formulae cited are pyrrolidonecarboxylic acid, benzenesulphonic acid, toluenesulphonic acid and also methanephosphonic and benzenephosphonic acid monoesters.

The diamines of the formula VI are also known compounds.

Polar organic solvents suitable for the process for the preparation of the compounds of the formula I are alcohols, ketones, ethers and esters and also mixtures thereof. Examples are: glycols, especially diethylene glycol, acetone, methyl ethyl ketone, dioxan, tetrahydrofuran, dipropyl ether, dibutyl ether, ethylene glycol dimethyl ether and the like. The more strongly polar solvents, such as dimethylformamide, dimethylacetamide and dimethylsulphoxide, are generally preferably employed.

The amount of solvent to be employed in the process is not critical as long as the amount is sufficient to dissolve the starting materials therein. In general, the reaction is carried out using 20 to 60 percent by weight solutions, based on the amount of the starting materials.

The complex compounds according to the invention are valuable curing agents for epoxide resins, and the complex compounds are employed in catalytic amounts.

The catalytic amounts used are in general 1–30, preferably 5–10, parts of the complex compound per 100 parts of epoxide resin.

The present invention thus also relates to the use of the complex compounds according to the invention as curing agents for epoxide resins.

All the known categories of epoxide resins are suitable as epoxide resins which can be cured by the complex compounds according to the invention. In particular, the epoxide resins are epoxide compounds which contain, on average, more than one glycidyl group, β-methylglycidyl group or 2,3-epoxycyclopentyl group bonded to a heteroatom (for example sulphur and preferably oxygen or nitrogen); preferred compounds are bis-(2,3-epoxycyclopentyl) ether; di- and poly-glycidyl ethers of polyhydric aliphatic alcohols, such as 1,4-butanediol, or polyalkylene glycols, such as polypropylene glycol; di- or poly-glycidyl ethers of cycloaliphatic polyols, such as 2,2-bis-(4-hydroxycyclohexyl)-propane; di- and poly-glycidyl ethers of polyhydric phenols, such as resorcinol, bis-(hydroxyphenyl)-methane, 2,2-bis(p-hydroxyphenyl)-propane (=diomethane), 2,2-bis-(4'-hydroxy-3',5'-dibromophenyl)-propane or 1,1,2,2-tetracis-(p-hydroxyphenyl)-ethane, or of condensation products of phenols with formaldehyde which are obtained under acid conditions, such as phenol novolacs and cresol novolacs; di- and poly-(β-methylglycidyl) ethers of the abovementioned polyhydric alcohols or polyhydric phenols; polyglycidyl esters of polybasic carboxylic acids, such as phthalic acid, terephthalic acid, $\Delta^4$-tetrahydrophthalic acid and hexahydrophthalic acid; N-glycidyl derivatives of amines, amides and heterocyclic nitrogen bases, such as N,N-diglycidylaniline, N,N-diglycidyltoluidine or N,N,N',N'-tetraglycidyl-bis-(p-aminophenyl)-methane; triglycidyl isocyanurate; N,N'-diglycidylethyleneurea; N,N'-diglycidyl-5,5-dimethylhydantoin and N,N'-diglycidyl-5-isopropylhydantoin; and N,N'-diglycidyl-5,5-dimethyl-6-isopropyl-5,6-dihydro-uracil.

Further suitable epoxide compounds are alicyclic diepoxides, such as vinylcyclohexane dioxide, limonene dioxide, dicyclopentadiene dioxide and ethylene glycol bis-(3,4-epoxytetrahydrocyclopentadien-8-yl)-glycidyl ether, and also compounds containing two epoxycyclohexyl radicals, such as diethylene glycol bis-(3,4-epoxycyclohexanecarboxylate), bis-(3,4-epoxycyclohexylmethyl) succinate, 3',4'-epoxy-6'-methylcyclohexylmethyl-3,4-epoxy-6-methyl-cyclohexane-carboxylate and 3',4'-epoxy-hexahydrobenzal-3,4-epoxycyclohexane-1,1-dimethanol.

In the following examples parts are by weight: percentages are by weight unless stated otherwise.

Preparation of the metal salt/amine complexes

EXAMPLE 1

(Complex A)

644.4 g (1.8 mol) of zinc pyrrolidone-5-carboxylate are reacted with 146.8 g (1.8 mol+10% excess) of 1,3-diaminopropane in 2,000 ml of dimethylformamide for 40 minutes at 128°–129° C. in a glass flask provided with a stirrer, a thermometer and a reflux condenser. The white suspension is then cooled to 5° C. and filtered and the residue is washed with dimethylformamide and diethyl ether. The residue is dried at 80° C./40 mm Hg and this yields 628 g (88.2% of theory) of a white, crystalline amine complex which melts at 212°–213° C., with decomposition.

| Elementary analysis: | |
|---|---|
| calculated | found |
| 39.46% C | 39.48% C |
| 5.60% H | 5.70% H |
| 14.16% N | 14.26% N |
| 16.52% Zn | 16.00% Zn |

The C$^{13}$- and H-NMR spectra are in accord with the following structure:

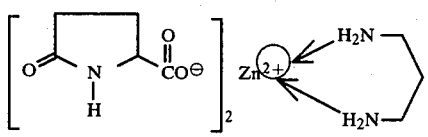

EXAMPLE 2

(Complex B)

9.64 g (0.03 mol) of zinc pyrrolidone-5-carboxylate and 4.92 g (0.03 mol+5% excess) of N-cyclohexyl-1,3-diaminopropane are reacted for 1 hour in 30 ml of dimethylformamide at 80° C. After the reaction has ended, the reaction mixture is cooled to 5° C. and is stirred for 1 hour at this temperature. The suspension is then filtered, the residue is washed with dimethylformamide and diethyl ether and the filter residue is dried at 60° C. in vacuo. This yields 9.9 g (68.4% of theory) of a white, crystalline amine complex which has a melting point of 178.9°-181.1° C.

| Elementary analysis: | |
|---|---|
| calculated | found |
| 47.32% C | 47.10% C |
| 6.69% H | 6.88% H |
| 11.62% N | 11.61% N |
| 13.55% Zn | 13.45% Zn |
| 0.93% H$_2$O | 0.93% H$_2$O |

The C$^{13}$- and H-NMR spectra are in agreement with the following structure:

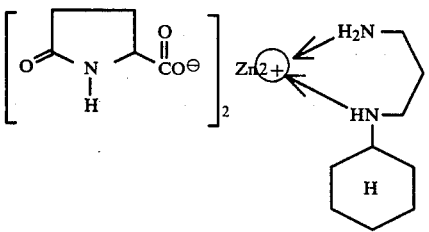

EXAMPLE 3

(Complex C)

Analogously to Example 1, 35.76 g (0.1 mol) of a zinc pyrrolidone-5-carboxylate and 18.08 g (0.1 mol+10% excess) of N-benzyl-1,3-diaminopropane in 100 ml of n-butanol are reacted for 1 hour and 37 minutes at 65°-100° C. After the reaction mixture has cooled to room temperature and diethyl ether has been added, the crystalline precipitate which has separated out is isolated by filtration and the filter residue is dried at 80° C. in vacuo. This yields 34.4 g (70.1% of theory) of a white, crystalline amine complex which melts at 160°-163° C.

| Elementary analysis: | |
|---|---|
| calculated | found |
| 48.97% C | 49.14% C |
| 5.75% H | 5.85% H |
| 11.42% N | 11.50% N |
| 13.32% Zn | 13.0% Zn |

| Elementary analysis: | |
|---|---|
| calculated | found |
| 0.96% H$_2$O | 0.96% H$_2$O |

According to the analysis, the compound has the following structure:

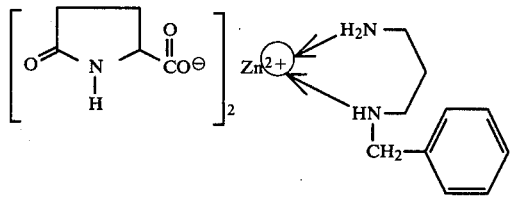

EXAMPLE 4

(Complex D)

16.2 g (0.05 mol) of zinc pyrrolidone-5-carboxylate (contains 0.73% by weight of water), 7.2 g (0.05 mol+5% excess) of 1,3-bis-(aminomethyl)-benzene and 80 ml of dimethylformamide are stirred for 1 hour and 20 minutes at 100°-129° C., during which time the amine complex formed goes only partially into solution. After the reaction has ended, the reaction mixture is cooled to room temperature and filtered. After drying the filter residue at 80° C. in vacuo, 20.4 g (89.1% of theory) of a white crystalline amine complex which decomposes at 241°-243° C. are obtained.

| Elementary analysis: | |
|---|---|
| calculated | found |
| 47.23% C | 47.34% C |
| 5.28% H | 5.15% H |
| 12.24% N | 12.24% N |
| 14.28% Zn | 14.0% Zn |

The C$^{13}$- and H-NMR spectra are compatible with the following structure:

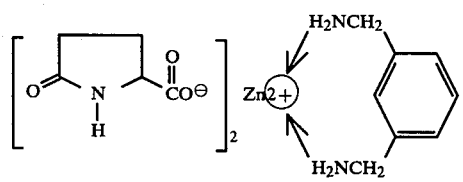

EXAMPLE 5

(Complex E)

In the manner described in Example 1, 35.76 g (0.1 mol) of zinc pyrrolidone-5-carboxylate (contains 6.35% by weight of H$_2$O) and 23.76 g (0.1 mol+5% excess) of 1,3-diamino-1,3-diphenylpropane in 200 ml of isopropyl alcohol are reacted for 1 hour and 15 minutes at 80° C. After the reaction has ended, the reaction mixture is cooled to 5° C., 80 ml of isopropanol are added and the crystal slurry is filtered off. The filter residue is dried at 80° C. in vacuo and this yields 46.7 g (84.0% of theory) of a white, crystalline amine complex which melts at 184°-198° C. with decomposition. The amine content is 3.60 equivalents of amino groups/kg (100% of theory).

| Elementary analysis: | |
|---|---|
| calculated | found |
| 54.00% C | 53.68% C |
| 5.62% H | 5.48% H |
| 10.08% N | 10.17% N |
| 11.76% Zn | 11.65% Zn |
| 1.46% $H_2O$ | 1.46% $H_2O$ |

According to the $C^{13}$-NMR spectrum, the amine complex has the following structure:

$$\left[ \begin{array}{c} O \\ \parallel \\ O \diagdown C \diagup N \diagdown CO^{\ominus} \\ H \end{array} \right]_2 Zn^{2+} \begin{array}{c} H_2N \diagdown \\ \\ H_2N \diagup \end{array} \diagdown \diagup \begin{array}{c} \text{Ph} \\ \\ \text{Ph} \end{array}$$

EXAMPLE 6

(Complex F)

238 g (0.8 mol) of the zinc salt of succinic acid monoamide and 62.3 g of 1,3-diaminopropane in 1,200 ml of methanol are reacted for 1 hour at 66° C. The reaction mixture is then cooled to 5° C. and filtered. The residue is dried at 80° C. in vacuo and 278.7 g (93.7% of theory) of the desired compound are obtained. The white, crystalline amine complex melts at 165°–168° C. and the amine content is 5.28 equivalents of amino group/kg (98.0% of theory).

| Elementary analysis: | |
|---|---|
| calculated | found |
| 35.55% C | 35.81% C |
| 5.97% H | 5.99% H |
| 15.07% N | 15.09% N |
| 17.59% Zn | 17.35% Zn |

The $C^{13}$- and H-NMR spectra are in agreement with the following structure:

$$\left[ H_2N-\overset{O}{\underset{\parallel}{C}}-CH_2CH_2-\overset{O}{\underset{\parallel}{C}}-O^{\ominus} \right]_2 Zn^{2+} \begin{array}{c} H_2N \diagdown \\ \\ H_2N \diagup \end{array}$$

EXAMPLE 7

(Complex G)

A mixture of 307.2 g (0.75 mol) of the zinc salt of succinic acid mono-N-butylamide and 58.35 g (0.75 mol+5% excess) of 1,3-diaminopropane in 1,000 ml of isopropyl alcohol is reacted for 1 hour and 10 minutes at 83° C. The turbid solution is then filtered hot and 1.5 liters of ether are added to the clear filtrate at a temperature of 65° C., with vigorous stirring. The mixture is cooled to about 5° C., the suspension is filtered and the filter residue is dried at 80° C. in vacuo. This yields 296.8 g (81.8% of theory) of a white, crystalline amine complex which melts at 167.2°–167.7° C.

| Elementary analysis: | |
|---|---|
| calculated | found |
| 47.16% C | 47.10% C |
| 7.92% H | 7.84% C |
| 11.58% N | 11.80% N |
| 13.51% Zn | 13.40% Zn |

The $C^{13}$- and H-NMR spectra are compatible with the following structure:

$$\left[ CH_3(CH_2)_3NH-\overset{O}{\underset{\parallel}{C}}-CH_2-CH_2-\overset{O}{\underset{\parallel}{C}}O^{\ominus} \right]_2 Zn^{2+} \begin{array}{c} H_2N \diagdown \\ \\ H_2N \diagup \end{array}$$

EXAMPLE 8

(Complex H)

A suspension consisting of 15.0 g (0.05 mol) of Zn ureidoacetate (zinc hydantoate) and 5.6 g (0.05 mol+50% excess) of 1,3-diaminopropane in 150 ml of methanol is stirred at 64° C. for 23 hours. The hot reaction mixture is then filtered and the filter residue is washed well with methanol and dried at 80° C. in vacuo. This yields 15.9 g (82.6% of theory) of the amine complex which has a melting point of 183°–184° C.

| Elememtary analysis: | |
|---|---|
| calculated | found |
| 28.06% C | 28.22% C |
| 5.59% H | 5.27% H |
| 21.82% N | 21.62% N |
| 3.00% $H_2O$ | 3.00% $H_2O$ |
| 16.97% Zn | 16.60% Zn |

The analysis agrees with the following structure:

$$\left[ H_2N-\overset{O}{\underset{\parallel}{C}}-NH-CH_2-\overset{O}{\underset{\parallel}{C}}-O^{\ominus} \right]_2 Zn^{2+} \begin{array}{c} H_2N \diagdown \\ \\ H_2N \diagup \end{array}$$

EXAMPLE 9

(Complex I)

10.0 g (0.025 mol) of zinc benzenesulphonate and 2.04 g (0.025 mol+10% excess) of 1,3-diaminopropane in 30 ml of methanol are reacted for 3 hours at 66° C. After the reaction has ended, the clear solution is concentrated in vacuo at 60° C. in a rotary evaporator and the residue is mixed vigorously with ether. The resulting suspension is filtered and the filter residue is dried in vacuo at 60° C.

Yield of pure product: 10.7 g (93.4% of theory)

The white, crystalline amine complex melts at 266.5°–273° C.

| Elementary analysis: | |
|---|---|
| calculated | found |
| 39.31% C | 39.58% C |
| 4.40% H | 4.73% H |

| Elementary analysis: | |
|---|---|
| calculated | found |
| 6.11% N | 6.35% N |
| 13.99% S | 14.36% S |
| 14.26% Zn | 13.9% Zn |
| 0.98% H₂O | 0.98% H₂O |

The compound has the following structure:

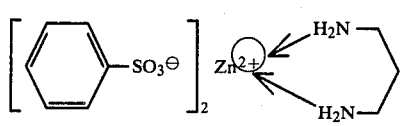

EXAMPLE 10

(Complex K)

14.17 g (0.05 mol) of the zinc salt of monomethyl methanephosphonate and 4.08 g (0.05 mol+10% excess) of 1,3-diaminopropane in 50 ml of isopropanol are stirred for 4 hours and 50 minutes at 84° C. After the reaction has ended, the clear solution is concentrated in vacuo at 80° C. in a rotary evaporator. The residue is then dried to constant weight at 60° C./0.1 mm Hg. This yields 18.1 g (100% of theory) of a highly viscous, yellowish amine complex which has the following analytical data.

| Elementary analysis: | |
|---|---|
| calculated | found |
| 23.27% C | 23.57% C |
| 6.14% H | 6.95% H |
| 7.75% N | 7.26% N |
| 17.15% P | 16.7% P |
| 18.09% Zn | 17.5% Zn |
| 1.04% H₂O | 1.04% H₂O |

The analytical data and the H-NMR spectrum are in accord with the following structure:

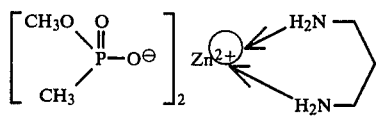

EXAMPLE 11

(Complex L)

Analogously to Example 1, 238 g (0.8 mol) of the Zn salt of N-acetylglycine, 65.2 g (0.8 mol+10% excess) of 1,3-diaminopropane and 800 ml of dimethylformamide are reacted for 1 hour and 10 minutes at 100°-110° C. and the reaction mixture is then worked up according to Example 1. This yields 264.1 g (88.8% of theory) of a white, crystalline amine complex which melts at 163°-164° C.

| Elementary analysis: | |
|---|---|
| calculated | found |
| 35.55% C | 35.59% C |
| 5.97% H | 6.15% H |
| 15.07% N | 14.94% N |

| Elementary analysis: | |
|---|---|
| calculated | found |
| 17.59% Zn | 17.45% Zn |

The H-NMR spectrum is in accord with the following structure:

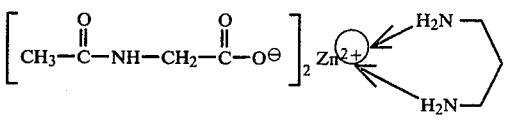

EXAMPLE 12

(Complex M)

A mixture of 17.9 g (0.05 mol) of Zn pyrrolidone-5-carboxylate, 6.39 g (0.055 mol) of 1,6-hexamethylenediamine and 50 ml of dimethylformamide is reacted for 1 hour at 110°-132° C. The suspension is then cooled to room temperature and filtered and the filter residue is dried in vacuo at 80° C. This yields 20.53 g (93.8% of theory) of a white, crystalline amine complex which decomposes at 204°-207° C.

| Elementary analysis: | |
|---|---|
| calculated | found |
| 43.90% C | 43.90% C |
| 6.45 H | 6.53% H |
| 12.80% N | 12.87% N |
| 14.93% Zn | 14.30% Zn |

The amine complex has the following structure:

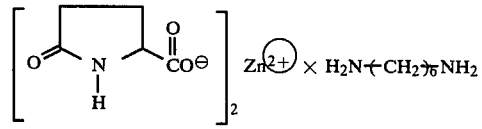

EXAMPLE 13

(Complex N)

162 g (0.5 mol) of Zn pyrrolidone-5-carboxylate (contains 0.7% of water of crystallisation), 49.6 g (0.5 mol+10% excess) of 1,3-diaminopropan-2-ol and 500 ml of methanol are allowed to react for 2 hours and 45 minutes at 64° C. and the reaction mixture is then cooled to 22° C. and stirred at room temperature for 16 hours. The crystal slurry is filtered off with suction and washed with methanol and the filter residue is dried in vacuo at 80° C. This yields 163.5 g (79.4% of theory) of a white, crystalline amine complex which melts and decomposes at 181° C.

| Elementary analysis: | |
|---|---|
| calculated | found |
| 37.93% C | 38.15% C |
| 5.39% H | 5.56% H |
| 13.61% N | 13.68% N |
| 15.88% Zn | 15.30% Zn |

Structure:

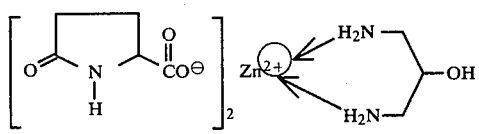

EXAMPLE 14

(Complex O)

24.5 g (0.05 mol) of Zn 6-succinimidyl-hexanecarboxylate, 4.1 g (0.05 mol+10% excess) of 1,3-diaminopropane and 80 ml of methanol are reacted in accordance with Example 1 for 50 minutes at 66° C. and the reaction mixture is then worked up analogously to Example 1. This yields 25.6 g (90.8% of theory) of a white, crystalline amine complex which melts at 141°–142.5° C.

Elementary analysis:

| calculated | found |
|---|---|
| 48.76% C | 48.59% C |
| 6.76% H | 6.84% H |
| 9.88% N | 9.86% N |
| 0.47% $H_2O$ | 0.47% $H_2O$ |
| 11.54% Zn | 11.65% Zn |

The H-NMR spectrum agrees with the following structure:

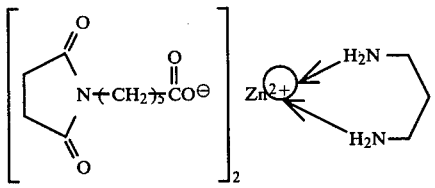

EXAMPLE 15

(Complex P)

27.1 g (0.05 mol) of Zn 6-(3',4'-dimethylmaleimido)-hexanecarboxylate, 4 mg (0.05 mol+10% excess) of 1,3-diaminopropane and 50 ml of methanol are reacted for 2 hours and 10 minutes at 67° C. The reaction mixture is concentrated at 60° C. and under a water pump vacuum in a rotary evaporator and the residue is taken up in 100 ml of diethyl ether. The crystal slurry is filtered off with suction and the filter residue is dried at 60° C. and 40 mm Hg and yields 28.8 g (93.5% of theory) of a crystalline amine complex which has a melting point of 97° C.

Elementary analysis:

| calculated | found |
|---|---|
| 52.41% C | 52.20% C |
| 6.84% H | 6.97% H |
| 9.06% N | 9.47% N |
| 0.44% $H_2O$ | 0.44% $H_2O$ |
| 10.57% Zn | 10.40% Zn |

According to the H-NMR spectrum, the amine complex has the following structure:

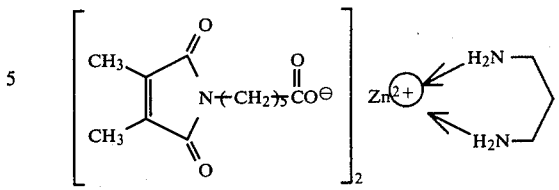

EXAMPLE 16

A suspension of 1.17 g (5 mmols) of Zn cyanoacetate, 0.41 g (5.0 mmols+10% excess) of 1,3-diaminopropane and 30 ml of methanol is reacted for 1 hour at 65° C. The reaction mixture is then cooled to room temperature and filtered and the filter residue is dried in vacuo at 40° C. This yields 1.3 g (84.5% of theory) of a white, crystalline amine complex which decomposes at about 160° C.

Elementary analysis:

| calculated | found |
|---|---|
| 35.02% C | 34.87% C |
| 4.57% H | 4.64% H |
| 18.15% N | 17.96% N |
| 21.17% Zn | 20.90% Zn |
| 0.36% $H_2O$ | 0.36% $H_2O$ |

The amine complex has the following structure:

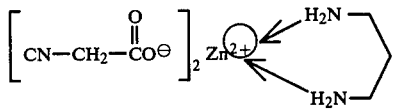

Use of the metal salt/amine complexes

Example I 100 parts of a liquid bisphenol A diglycidyl ether resin with an epoxide content of 5.2 equivalents/kg are warmed to 150° C. and 10 parts of the complex B prepared according to Example 2 are added, with stirring. After 5–10 minutes, a clear solution is obtained (solution A). This solution is compared, in respect of the storage stability and the characteristics of the shaped articles produced therefrom, with solution B which contains the standard latent curing agent boron trifluoride/-monoethylamine in place of complex B.

Solution B: 100 parts of the epoxide resin used above are warmed to 80° C. and 2 parts of boron trifluoride/-monoethylamine are added, with stirring.

| Assessment of the storage stability | | |
|---|---|---|
| Storage time at room temperature | Gel time at 120° C. (minutes) | |
| (days) | Solution A | Solution B |
| 0 | 74 | 74 |
| 5 | 68 (−8.1%) | 62 (−16.2%) |
| 20 | 61 (−17.6%) | 61 (−17.6%) |
| 40 | 60 (−18.9%) | 58 (−21.6%) |

The gel times were measured using amounts of about 0.5 g in each case, on a gel time plate.

The comparison shows that both solutions are virtually equivalent in respect of the storage stability and, moreover, have an identical reactivity at elevated temperature.

Shaped articles are produced from solutions A and B by means of curing. The characteristics of the cured moulded materials are given in Table I.

TABLE I

Characteristics of the molded materials produced from solution A and solution B

| Characteristics | Solution A | Solution B |
|---|---|---|
| Curing | 3 hours/120 + 1 hour/160 + 3 hours/200° C. | 4 hours/80 + 8 hours/140° C. |
| Flexural strength according to VSM* 77,103 [kg/cm$^2$] | 12.6 | 13.2 |
| Deflection according to VSM 77,103 [mm] | 6.3 | 4.1 |
| Impact strength according to VSM 77,103 [cmkg/cm$^2$] | 11.5 | 9.7 |
| Tensile shear strength according to VSM 77,101 [kg/mm$^2$] | 1.70 | 1.24 |
| Heat distortion point according to Martens DIN** 53,458 [°C.] | 128 | 65 |
| Absorption of water 1 hour/100° C. [%] | 0.24 | 0.51 |
| Dielectric loss factor tan δ 1% value [°C.] | 162 | 72 |
| 10% value [°C.] | 201 | 99 |

*VSM = Verein Schweizerischer Maschinenindustrieller
**DIN = Deutsche-Industrie-Norm As can be seen from the table, the moulded materials produced using the novel complex compound have significantly better values in respect of the heat distortion point, the absorption of water and the dielectric loss factor.

Comparison A

Use of a tertiary amine as the catalytic curing agent 100 parts of the epoxide resin used in Example I and 10 parts of tris-(dimethylaminomethyl)-phenol are mixed together at room temperature, a solution being obtained.

Assessment of the storage stability

The solution has gelled after a storage time of 30 minutes at room temperature.

Characteristics of the moulded materials

Cured shaped articles are obtained from the above solution after curing for 24 hours at 40° C. and 4 hours at 100° C.; these shaped articles have the following characteristics:

| | |
|---|---|
| Heat distortion point according to Martens DIN 53,458 | 94° C. |
| Absorption of water, 1 hour/100° C. | 0.52% |
| Dielectric loss factor tan δ 1% value | 101° C. |
| 10% value | 116° C. |

In a mixture with the epoxide resin, the tertiary amine is inferior to the novel complex compounds, both in respect of the storage stability and in respect of the characteristics of the moulded materials produced therefrom.

Comparison B

Use of different amounts of N-cyclohexyl-1,3-diaminopropane as the curing agent 100 parts of the bisphenol A diglycidyl ether used in Example I are mixed, at room temperature, with different amounts of the N-cyclohexyl-diaminopropane contained in the complex compound B, specifically, (a) with the stoichiometric amount (=27.6 parts) and
(b) with that amount which is contained in 10 parts of the complex compound B.

Processing and curing of these mixtures gave the following results:

(a) 100 parts of epoxide resin per 27.6 parts of N-cyclohexyl-1,3-diaminopropane This mixture has a very limited stability on storage. The mixture has gelled within 6 hours at room temperature and within 1.5 hours at 40° C. After extensive curing for 24 hours at 40° C. and 6 hours at 100° C., moulded materials are obtained which have the following characteristics:

| | |
|---|---|
| Martens value according to DIN 55,458 | 77° C. |
| Dielectric loss factor tan δ 1% value | 87° C. |
| 10% value | 99° C. |
| Absorption of water, 1 hour/100° C. | 0.46% |

(b) 100 parts of epoxide resin per 3.23 parts of N-cyclohexyl-1,3-diaminopropane This mixture has a good storage stability; however it is not curable but still remains liquid even after extensive curing for 6 hours at 200° C.

Comparison C

Use of a mixture of N-cyclohexyl-1,3-diaminopropane and zinc pyrrolidonecarboxylate as the catalytic curing agent 100 parts of the epoxide resin used in Example I are combined with 6.77 parts of zinc pyrrolidonecarboxylate and 3.32 parts of 1,3-diaminopropane, corresponding to the amount contained in 10 parts of complex compound B. The zinc pyrrolidonecarboxylate is first mixed intensively with the epoxide resin and the diamine is then added. At room temperature, the mixture is a dispersion containing very finely dispersed particles; this is in contrast to the homogeneous solution obtained in Example I.

After curing for 3 hours/120° C., 1 hour at 160° C. and 3 hours at 200° C., shaped articles are obtained which have the following characteristics:

| | |
|---|---|
| Martens value according to DIN 55,458 | 112° C. |
| Dielectric loss factor tan δ 1% value | 136° C. |
| 10% value | 183° C. |

This comparison shows that the use of a mixture of the individual components of the complex does not lead to a result equally as good as that obtained when the complex compound itself is used.

Comparison D

Use of the complex compound described in U.S. Pat. No. 2,819,233 (Complex I) as the curing agent for epoxide resins For comparison, a complex I is prepared in accordance with the instructions given under "Complex A"

in the U.S. Patent and is processed as in Example IV of the U.S. Patent.

Complex I: Zinc 2-ethylhexanoate is prepared from 1 mol of zinc oxide and 2 mols of 2-ethylhexanoic acid in 475 g of xylene. 1 mol of diethylenetriamine is added to this solution, with stirring, and the reaction is carried out for 35 minutes at 120° C. After drying at 50° C., the complex still contains about 5% of xylene and has a diethylenetriamine content of 6.44 equivalents/kg.

100 parts of the bisphenol A diglycidyl ether used in Example I of this specification are mixed with 20 parts of complex I, corresponding to the mixing ratio of 0.25 equivalent of active amino group per 1 epoxide equivalent which is given in Example IV of the U.S. Patent. The pot life of this formulation at 40° C. and up to 15,000 cP is 26 hours; this formulation has gelled within 4 days. Compared with this, a formulation consisting of the same epoxide resin and the complex compound B is stable on storage for at least 10 days at the same temperature.

The formulation containing complex I is cured for 2, 4 and 8 hours at 120° C. and the glass transition temperature ($T_g$) of the resulting products is measured using a differential thermo-analyser (DTA 2000 apparatus) from Mettler (Greifensee, Switzerland).

| Curing | $T_g$ |
|---|---|
| 2 hours/120° C. | 98° C. |
| 4 hours/120° C. | 99° C. |
| 8 hours/120° C. | 100° C. |

In all 3 cases, the samples are not completely cured, since a distinct exothermic subsequent reaction can be detected in the DTA thermograms. On curing for 2, 4 and 8 hours at 200° C., the following values are obtained:

| Curing | $T_g$ |
|---|---|
| 2 hours/200° C. | 109° C. |
| 4 hours/200° C. | 110° C. |
| 8 hours/200° C. | 109° C. |

The $T_g$ has risen, but here also exothermic subsequent reactions are detected in all 3 cases.

In comparison, the formulation consisting of the same epoxide resin and the complex compound B according to the invention has completely cured after 6 hours at 200° C. and has a $T_g$ of 165° C.

EXAMPLE II 100 parts of the bisphenol A diglycidyl ether used in Example I, 10 parts of the complex compound A and 1.5 parts of "Aerosil" (99.8% pure $SiO_2$) are mixed intensively in a three-roll mill. The dispersion obtained in this way is examined in respect of its storage stability and film characteristics.

One portion of the dispersion is stored at 40° C. and the tensile shear strength on "Anticorrodal B" (aluminium alloy) as a function of the storage time is followed. For this purpose, samples are taken at specific intervals from the stored stock dispersion and these samples are used to produce tensile shear strength test pieces. Curing is carried out for 10 minutes at 150° C. and 4 hours at 160° C. Before storage, the dispersion has a tensile shear strength value (according to VSM 77,101) of 1.9 kg/mm². After storing for 120 days at 40° C. there has been no significant change in this initial value.

Under the same curing conditions, films 50μ thick are produced on sheet aluminium and the mechanical properties and resistance to chemicals of these films are measured.
Erichsen deep drawing (DIN 53,156) = 10 mm
Impact Erichsen value (drop height/2 kg hammer) = 90 cm In order to determine the resistance to chemicals, one drop of acetone, one drop of distilled $H_2O$, one drop of 5 N $H_2SO_4$ and one drop of 5 N NaOH are left covered on the 50μ film for 1 hour.

At the end of this time, it is found, by visual assessment, that the film has not been attacked by the chemicals.

EXAMPLE III 100 parts of a halogen-containing, solid epoxide resin which is based on bisphenol A and has an epoxide content of 2.1 equivalents/kg are melted at 130°–140° C. and the melt is then cooled to about 100° C.

5 parts of the complex compound A are dissolved at 150°–155° C. in 65 parts of tetrahydrofuryl alcohol and the solution is cooled to 80° C. The solution is added to the molten epoxide resin and the whole is stirred well. A clear, slightly brown solution is obtained which at 25° C. has a desired impregnating viscosity of 130–140 cP.

An 18 cm broad web of glass fabric of "Quality CS 7628" from CLARK-SCHVEBEL S.A. is drawn with the aid of a drawing device through an impregnating vat containing the impregnating solution described above. The excess impregnating solution is removed by hanging up the impregnated web. The impregnated glass fabric is mounted on a special frame and dried for 8 minutes at 170° C. The dried web is cut into pieces having dimensions of 15×15. 10 of these layers are compressed in a laboratory press under a maximum pressure of 10 tonnes for 60 minutes at 200° C. to give a laminate.

This laminate has a resin content of 41% by weight and has the following characteristics.

| | |
|---|---|
| Flexural strength according to ISO-R*** 178 [kg/mm²] | = 53.2 |
| Edge fibre elongation according to ISO-R 178 [%] | = 3.0 |
| Impact strength according to ISO-R 179 [cmkg/cm²] | = 78.9 |
| Absorption of water: | |
| 4 days/25° C. [%] | = 0.09 |
| 1 hour/100° C. [%] | = 0.20 |
| Dielectric loss factor | |
| tan δ 1% value [°C.] | = 103 |
| 10% value [°C.] | = 146 |

***Iso-R = International Standards Organisations Recommendations

EXAMPLE IV 100 parts of the bisphenol A diglycidyl ether used in Example I, 10 parts of the complex compound F and 1.5 parts of "Aerosil" are mixed intensively in a three-roll mill. The resulting dispersion has a good storage stability similar to that of Example II, specifically: Initial value for the tensile shear strength (VSM 77,101) after curing for 1 hour/180° C.: 1.97 kg/mm².

After storing for 152 days at room temperature and 35 days at 40° C., no significant decrease in the tensile shear strength could be detected.

When the test to determine the resistance to chemicals is carried out (method as in Example II), a very good result is again obtained. The reagents acetone, chlorobenzene, water, 5 N NaOH and 5 N H$_2$SO$_4$ show no action whatsoever on the test film.

EXAMPLE V 100 parts of the bisphenol A diglycidyl ether used in Example II, 10 parts of the complex compound D and 1.5 parts of "Aerosil" are mixed intensively in a three-roll mill. The resulting dispersion has a good storage stability similar to that of Example II.

Initial value for the tensile shear strength (VSM 77,101) after curing for 1 hour/200° C: 1.75 kg/mm$^2$.

After storing for 152 days at room temperature, no significant decrease in the tensile shear strength is found.

When the test to determine the resistance to chemicals is carried out (see Example 10 for the method, assessment and the like), a very good result is obtained, as in the preceding example. The reagents acetone, chlorobenzene, water, 5 N NaOH and 5 N H$_2$SO$_4$ show no action whatsoever on the test film.

EXAMPLE VI 100 parts of the bisphenol A diglycidyl ether used in Example I are taken and 10 parts of the complex compound K and 25 parts of methyl ethyl ketone are added. The mixture is stirred and at about 50° C. a clear solution is obtained. The viscosity of the impregnating solution is 144 cP at 25° C.

The prepreg and laminate production is carried out in virtually the same manner as described in Example III.

| | |
|---|---|
| Drying conditions for the impregnated glass fabric (prepreg): | 9 minutes/160° C. |
| Curing in the press: | 60 minutes/200° C. |

The laminate has a resin content of 44.3% by weight and has the following characteristics:

| | |
|---|---|
| Flexural strength according to ISO-R 178 [kg/mm$^2$] | = 51.2 |
| Edge fibre elongation according to ISO-R 178 [%] | = 2.8 |
| Impact strength according to ISO-R 179 [cmkg/cm$^2$] | = 66.7 |
| Absorption of water: | |
| 4 days/25° C. [%] | = 0.16 |
| 1 hour/100° C. [%] | = 0.23 |
| Dielectric loss factor | |
| tan δ 1% value [°C.] | = 104 |
| 10% value [°C.] | = 152 |

What is claimed is:

1. A storage-stable, heat-curable mixture comprising
(a) an epoxide compound having on average more than one epoxy group per molecule and
(b) 1 to 30 parts per 100 parts by weight of the epoxide compound (a) of a metal/amine complex of the formula

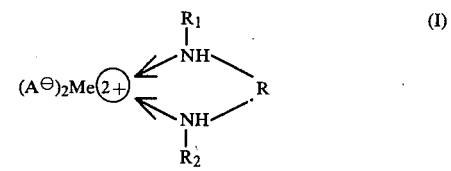

wherein A$^\ominus$ is an anion of the formula II $$R_3-NH-CO-Y_1-COO^\ominus \qquad (II)$$

in which R$_3$ is —H, alkyl having 1 to 4 C atoms, cyclopentyl or cyclohexyl and Y$_1$ is a radical of the formulae —CH$_2$)$_x$, in which x=2 or 3, or —CH=CH— or an anion of the formulae

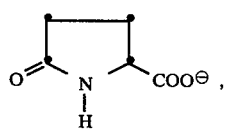

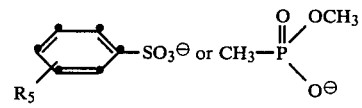

in which R$_5$ is —H or methyl, Me $(2+)$ is a divalent metal cation and, if R$_1$ and R$_2$ are each a hydrogen atom, R is one of the following radicals —CH$_2$-(-CH$_2$)$_p$- in which p=a number from 1 to 6,

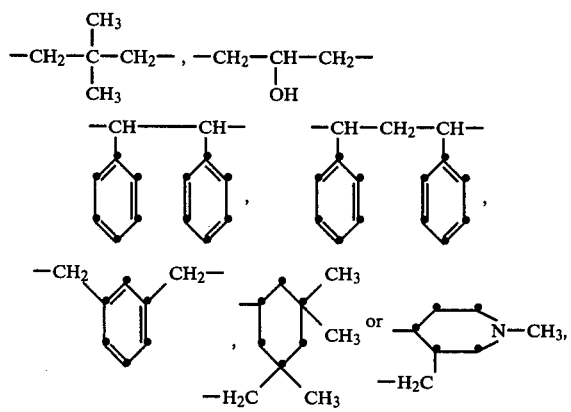

and, if R$_1$ is a hydrogen atom and R$_2$ is an alkyl having 1 to 4 atoms, cyclohexyl, benzyl, 2-aminoethyl or 3-aminopropyl, or if R$_1$ and R$_2$ are each an alkyl having 1 to 4 C atoms, cyclohexyl or benzyl, R is an ethylene or propylene radical.

2. A mixture according to claim 1, comprising 5 to 10 parts of the metal/amine complex of formula I per 100 parts by weight of the epoxide compound.

3. A mixture according to claim 1, comprising a metal/amine complex of formula I, wherein A $\ominus$ is an anion of the formula II in which R$_3$ is —H, alkyl having 1 to 4 C atoms or cyclohexyl and Y$_1$ is a radical of the formula -(-CH$_2$)$_x$, in which x is 2 or 3, or an anion of the formulae

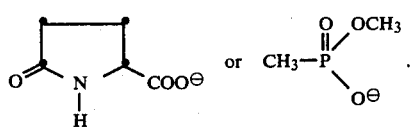 or 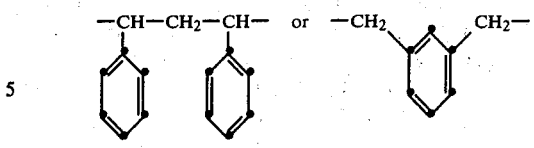

4. A mixture according to claim 1, comprising a metal/amine complex of formula I, wherein Me ②⁺ is a divalent metal cation of Zn, Co, Cu, Ni or Cd.

5. A mixture according to claim 1, comprising a metal/amine complex of the formula I, wherein $R_1$ and $R_2$ are each a hydrogen atom and R is a radical of the formulae $-CH_2-CH_2)_p$, in which p=a number from 1 to 5, or in which $R_1$ is a hydrogen atom and $R_2$ is cyclohexyl, benzyl, 2-aminoethyl or 3-aminopropyl and R is an ethylene or propylene radical.

6. A mixture according to claim 1, comprising a metal/amine complex of formula I, wherein $R_1$ and $R_2$ are each a hydrogen atom and R is a radical of the formula $-CH_2-(CH_2)_p$, in which p=a number from 1 to 3, or in which $R_1$ is a hydrogen atom and $R_2$ is a cyclohexyl or benzyl, 2-aminoethyl or 3-aminopropyl and R is an ethylene or propylene radical.

* * * * *